(12) United States Patent
Clark, Jr.

(10) Patent No.: US 8,657,770 B1
(45) Date of Patent: Feb. 25, 2014

(54) SPINAL STRETCHING AND DECOMPRESSION DEVICE

(76) Inventor: Milas G. Clark, Jr., Los Angeles, CA (US)

( * ) Notice: Subject to any disclaimer, the term of this patent is extended or adjusted under 35 U.S.C. 154(b) by 158 days.

(21) Appl. No.: 13/134,201

(22) Filed: Jun. 1, 2011

(51) Int. Cl.
*A61F 5/00* (2006.01)

(52) U.S. Cl.
USPC ............................................. 602/19; 602/32

(58) Field of Classification Search
USPC ............. 602/19, 32; 128/99–105.1, 874–875; 2/79, 81
See application file for complete search history.

(56) References Cited

U.S. PATENT DOCUMENTS

| | | | | |
|---|---|---|---|---|
| 1,870,356 A | * | 8/1932 | Davis et al. | 128/100.1 |
| 3,424,134 A | * | 1/1969 | Rosenblum | 182/3 |
| 5,027,833 A | * | 7/1991 | Calkin | 128/870 |
| 6,308,335 B1 | * | 10/2001 | Colorado | 2/81 |
| 7,833,182 B2 | * | 11/2010 | Hughes | 602/19 |
| 2003/0018287 A1 | | 1/2003 | Gilliam | |
| 2003/0098575 A1 | | 5/2003 | Schroth et al. | |

* cited by examiner

*Primary Examiner* — Michael A. Brown
(74) *Attorney, Agent, or Firm* — Albert O Cota

(57) ABSTRACT

A spinal stretching and decompression device (10) that is effective for treating a plurality of spinal disorders or lower back conditions, such as sciatica. The device (10) is worn around a person's mid-section, and encompasses the person's buttocks and crotch region, during an exercise or stretching session. There are two embodiments of the device (10) with both embodiments comprising a base support belt (12 or 112), a lower support unit (44) that is attached to the base support belt (12 or 112), a first side support belt (72) and a second side support belt (92). The two side support belts pass through loops on the base support belt (92) and each belt is secured together around a person's waist. The difference between the two embodiment is that the first embodiment elements are integrally attached, and the second embodiment elements are removably attached by multiple buckles.

15 Claims, 5 Drawing Sheets

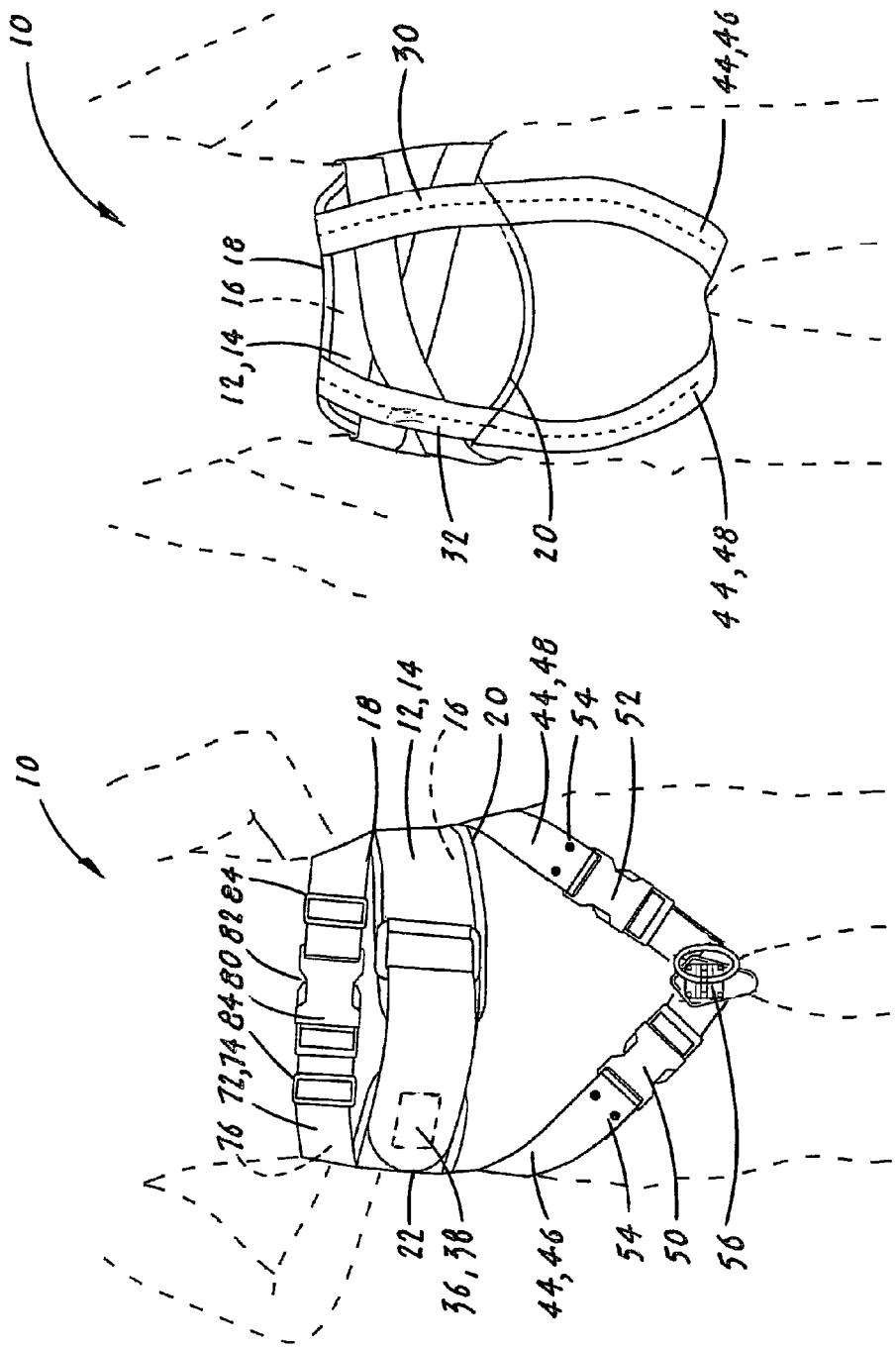

SPINAL STRETCHING AND DECOMPRESSION DEVICE

TECHNICAL FIELD

The invention generally pertains to devices and methods used during the performance of stretching exercises. More particularly to a device that facilitates stretching and decompression of a person's lower lumbar spine.

BACKGROUND ART

Some of the most prevalent problems that are experienced by 80% of all American people over the age of 40 are problems effecting or related to lower back pain. Back pain comes in two categories, medical (less than 4%) and mechanical (greater than 96%); for people that have these disorders it is known as mechanical spinal pathology. Some people are born with one or more spinal disorder problems, while other people develop problems as a result of an injury or simple aging.

Some of these problems are cause spinal instability; and are known as a herniated disc, degenerative joint disease, sciatica, facet syndrome and even spinal stenosis. Depending on the exact problem and the severity of the problem, there are several options available for treatment. Some problems can be alleviated by stretching and/or exercise, while other problems benefit from chiropractic treatment. For the most serious problems, surgery is the most typical solution. Although surgery may be effective, many doctors and most patients would rather use other non-invasive methods to solve a back pain problem.

As a result, there are many alternate options available. Most of these options include some type of stretching and/or decompressing capability. The ability of these devices to actually help a person suffering from a back or spine problem varies. Some devices have proven to be effective, while others are either ineffective or can even worsen a problem.

As technology improves, opportunities arise for creating a truly effective, easy-to-use device that can help a person who is suffering from a mild to serious back or spine problem. Ultimately, the most beneficial device would be capable of obtaining the some results of a successful surgery.

A search of the prior art did not disclose literature or patents that read directly on the claims of the instant invention. However, the following U.S. patents are considered related.

| PAT. NO. | INVENTOR | ISSUED |
| --- | --- | --- |
| Pub. No. 2003/0098575 | Schroth et al | 29 May 2003 |
| Pub. No. 2003/0018287 | Gilliam | 23 Jan. 2003 |

The publication number 2003/0098575 discloses a harness belt comprising a dual pelvis belt, two shoulder belts and two crotch belts. The belt segments of the pelvis belts as well as the shoulder belts can be joined by means of a belt tongue to a belt buckle. The crotch belts, by means of the buckle proximate loops surround the belt tongues of the belt segments of the pelvis belt and are secured in a circumferential direction against movement relative to the belt buckle. The belt tongues are configured with recesses adapted for the belt tongues in belt buckle. The loops are connected to the buckle proximate ends of the crotch belts at an obtuse angle.

The publication number 2003/0018287 discloses a traction device that utilizes a harness connected to the body of a patient. The harness is connected by a clip to a tether which passes through a ratchet pulley connected to a first end of a spring chamber. A second end of the spring chamber is connected to a support. As tension is applied to the tether, the ratchet pulley incrementally applies traction to the patient as a first spring housed within the spring chamber deflects with the application of force.

DISCLOSURE OF THE INVENTION

The invention discloses a device for stretching and/or decompressing a person's spine. The device is effective for treating a variety of spinal or lower back conditions such as sciatica. The device is worn around a person's mid-section, and encompasses the person's buttocks and crotch region, during an exercise or stretching session.

In its most basic design, the device is comprised of a base support belt, a lower support unit that is attached to the base support belt, a first side support belt, and a second side support belt. The two side support belts pass through loops on the base support belt and each belt is secured together around a persons' waist.

Once the device is placed on a person, various buckles are utilized to maintain the device on the person and allow the device to be comfortably adjusted to persons of various sizes ands shapes.

In view of the above disclosure, the primary object of the invention is to provide a spinal stretching and decompression device that can be utilized to aid a person who is experiencing a variety of spinal disorders or lower back conditions.

In addition to the primary object of the invention, it is also an object of the invention to provide a spinal stretching and decompression device that:

can be made of various materials,
    can be made in various sizes to accommodate small and large individuals, including children and adults,
    is easy to use,
    is easy to transport and store,
    can be used with other stretching and exercising equipment,
    is durable and long-lasting, and
    is cost effective from both a manufacturer's and consumer's point of view.

These and other objects and advantages of the present invention will become apparent from the subsequent detailed description of the preferred embodiment and the appended claims taken in conjunction with the accompanying drawings.

BRIEF DESCRIPTION OF THE DRAWINGS

FIG. 1 is a front elevational view of a spinal stretching and decompression device on the front of a person.

FIG. 2 is a rear elevational view of the spinal stretching and decompression device on the rear of a person.

BEST MODE FOR CARRYING OUT TILE INVENTION

Figure 3:
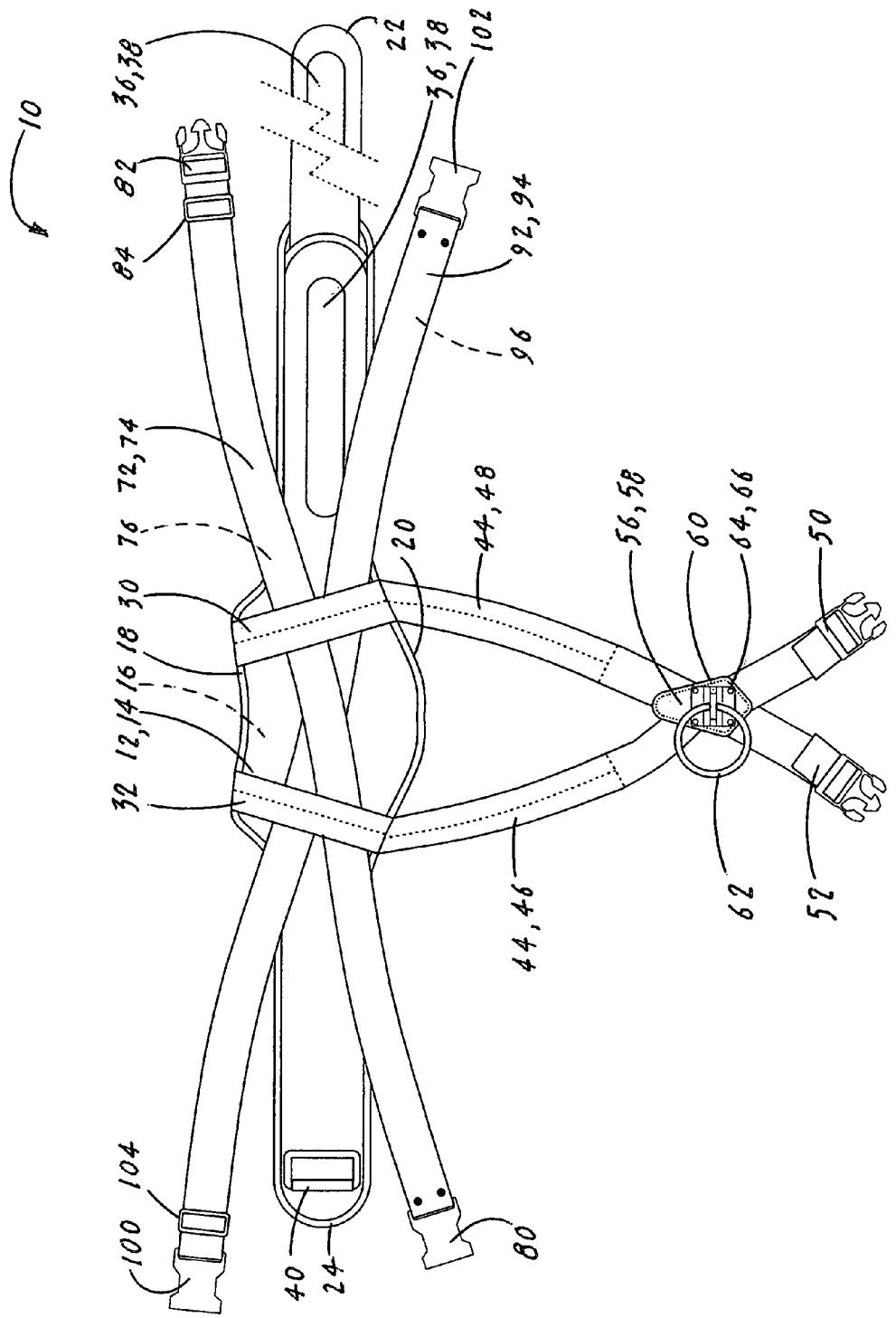
FIG. 3 is a front elevational view of the outer surfaces of the first embodiment of the spinal stretching and decompression device.

The best mode for carrying out the invention is presented in terms that disclose a preferred embodiment of a device for stretching and/or decompressing a person's lower lumbar spine. The device is effective for treating a plurality of spinal disorders or lower back conditions such as sciatica. The device is worn around a person's mid-section, and encompasses the person's buttocks and crotch region, during an exercise or stretching session.

The preferred embodiment of the device 10, as shown in FIG. 1-6, is comprised of the following major elements: a base support belt 12, a lower support unit 44, a first side support belt 72, and a second side support belt 92.

The base support belt 12, as shown in FIGS. 1-6, is comprised of an outer surface 14, an inner surface 16, an upper edge 18, a lower edge 20, a first end 22, a second end 24, a first (right) strap loop 30, a second (left) strap loop 32 and attachment means 36 which preferably comprise a hook and loop fastener 38 and a loop 40.

The lower support unit 44, as shown in FIGS. 1-6, is integrally attached to the base support belt 12, and is comprised of a first (right) strap 46, a second (left) strap 48, a first strap buckle 50, a second strap buckle 52, buckle attachment means 54 and a hitch ring assembly 56. As shown in FIGS. 1 and 3, the hitch ring assembly 56 has a hitch base 58, a hitch plate 60, a hitch ring 62, and an assembly attachment means 64 which preferably comprised at least two nuts and bolts 66.

Figure 4:
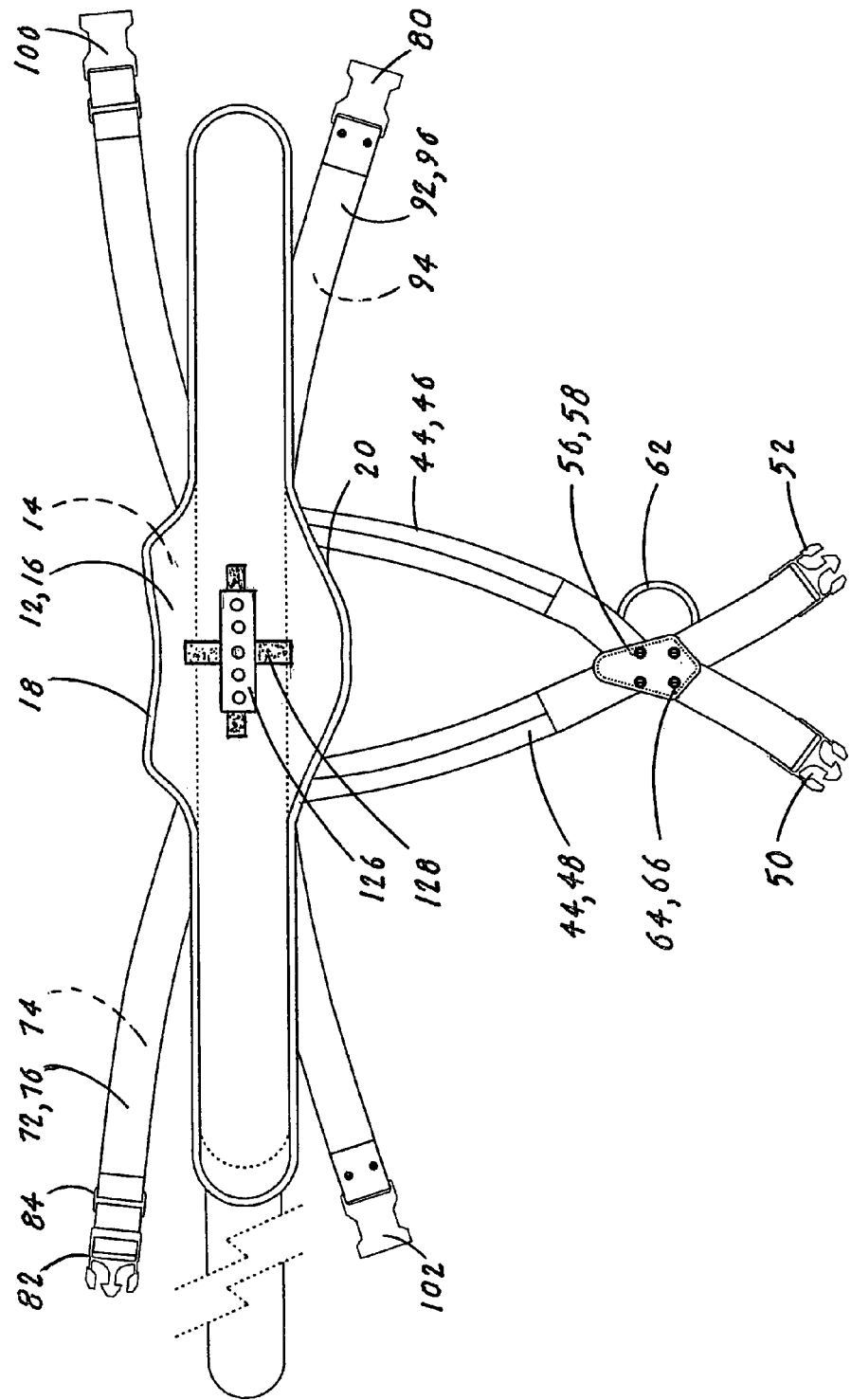
FIG. 4 is a front elevational view of the inner surface of the first embodiment of the spinal stretching and decompression device.

The first side support belt 72, as shown in FIGS. 2-4, is comprised of an outer surface 74, an inner surface 76, a first (right) buckle 80, a second (left) buckle 82, and buckle adjustment means 84.

The second side support belt 92, as shown in FIGS. 2-4, is essentially the same as the first side support belt 72 and is comprised of an outer surface 94, an inner surface 96, a first (right) buckle 100, a second (left) buckle 102, and buckle adjustment means 104.

All of the belts are made of a material that is selected from the group consisting of nylon, leather, or similar types of fabric, with nylon preferred. The buckles are comprised of two-inch heavy duty, quick-release, snap type, and as previously disclosed, the attachment means for attaching the buckles to the straps are comprised of a plurality of nuts, bolts, washers or rivets.

The device 10 is utilized in combination with stretching and/or exercising actions that include bending, lifting, and extending.

The device 10 is worn around a person's mid-section, and encompasses the person's buttocks and crotch region. The method for attaching the device 10 to a person is comprised of the following steps.

It should be noted that in order to clearly indicate the multiple attachments/connections of belt and buckles, letter designations in addition to numerical designations, are utilized.

1. Wrap the base support belt 12 around the person's waist and secure the first end 22 of the belt 12 to the second end 24 by use of the attachment means.

2. Wrap the first side support belt 72 around the base support belt 12, wherein the first side support belt 72 is inserted through the first belt loop 30 on the base support belt 12 and is secured by attaching the first buckle 80 to the second buckle 82.

3. Wrap the second side support belt 92 around the base support belt 12, wherein the second side support belt 92 is inserted through the second belt loop 32 on the base support belt 12 and is secured by attaching the first buckle 100 to the second buckle 102.

4. Wrap the lower support unit 44 around and under a person's buttocks and groin. Attach a buckle designated A to a buckle designated E. Then, attach a buckle designated C to a buckle designated F, and a buckle designated B to a buckle designated D.

5. Adjust the device 10 for a secure and comfortable fit.

In a second embodiment, the device 10 utilizes additional buckles. The second embodiment, as shown in FIGS. 5 and 6, comprises the same major belts as the first embodiment, including a base support belt 112, a lower support unit 152, a first side support belt 194 and a second side support belt 210.

Figure 5:
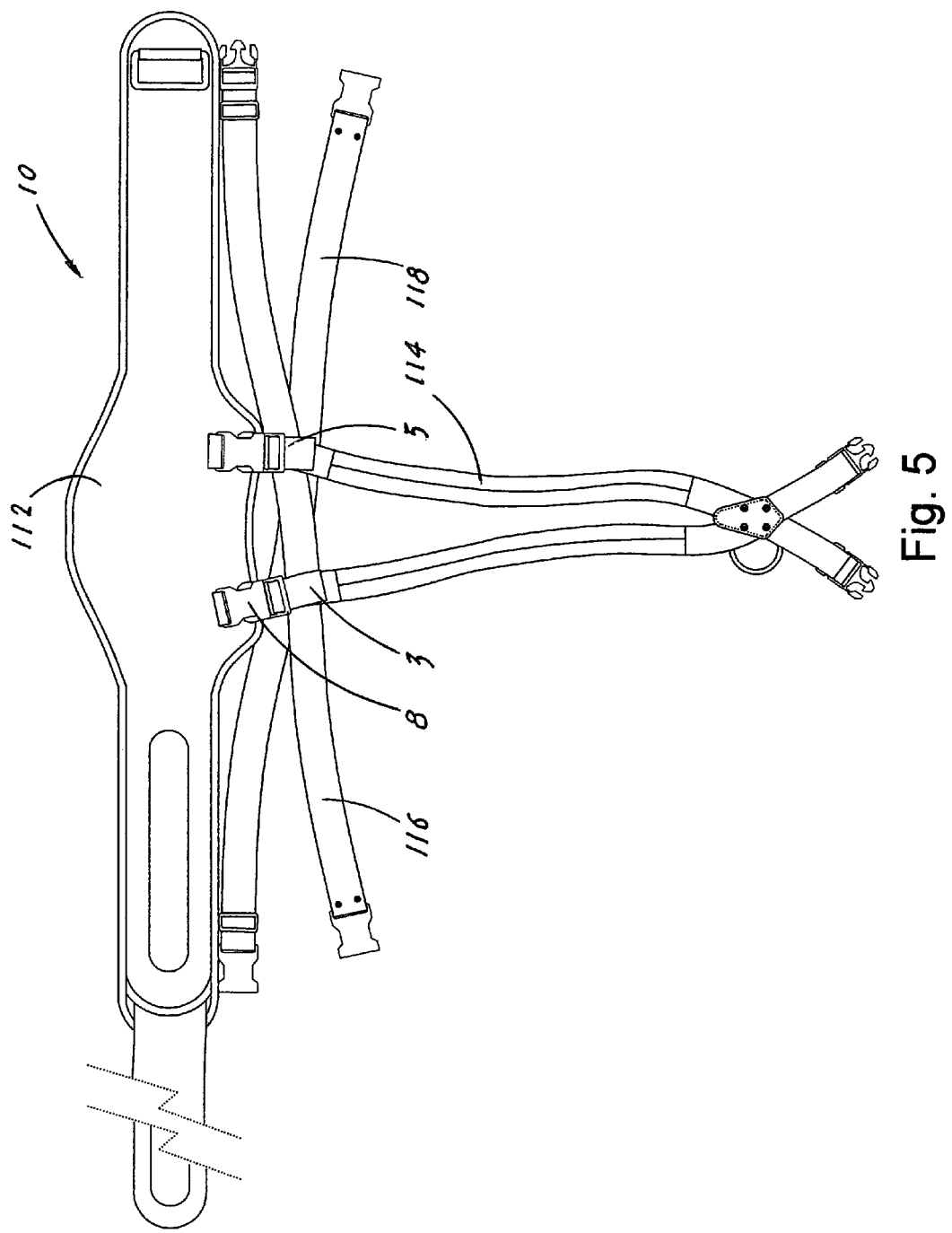
FIG. 5 is a front elevational view of the outer surfaces of the second embodiment of the spinal stretching and decompression device.

As shown in FIG. 5, the base support belt 112 further comprises a buckle designated number 5, a buckle designated number 6, a buckle designated number 7, a buckle designated number 8, and buckle attachment means 146.

Figure 6:
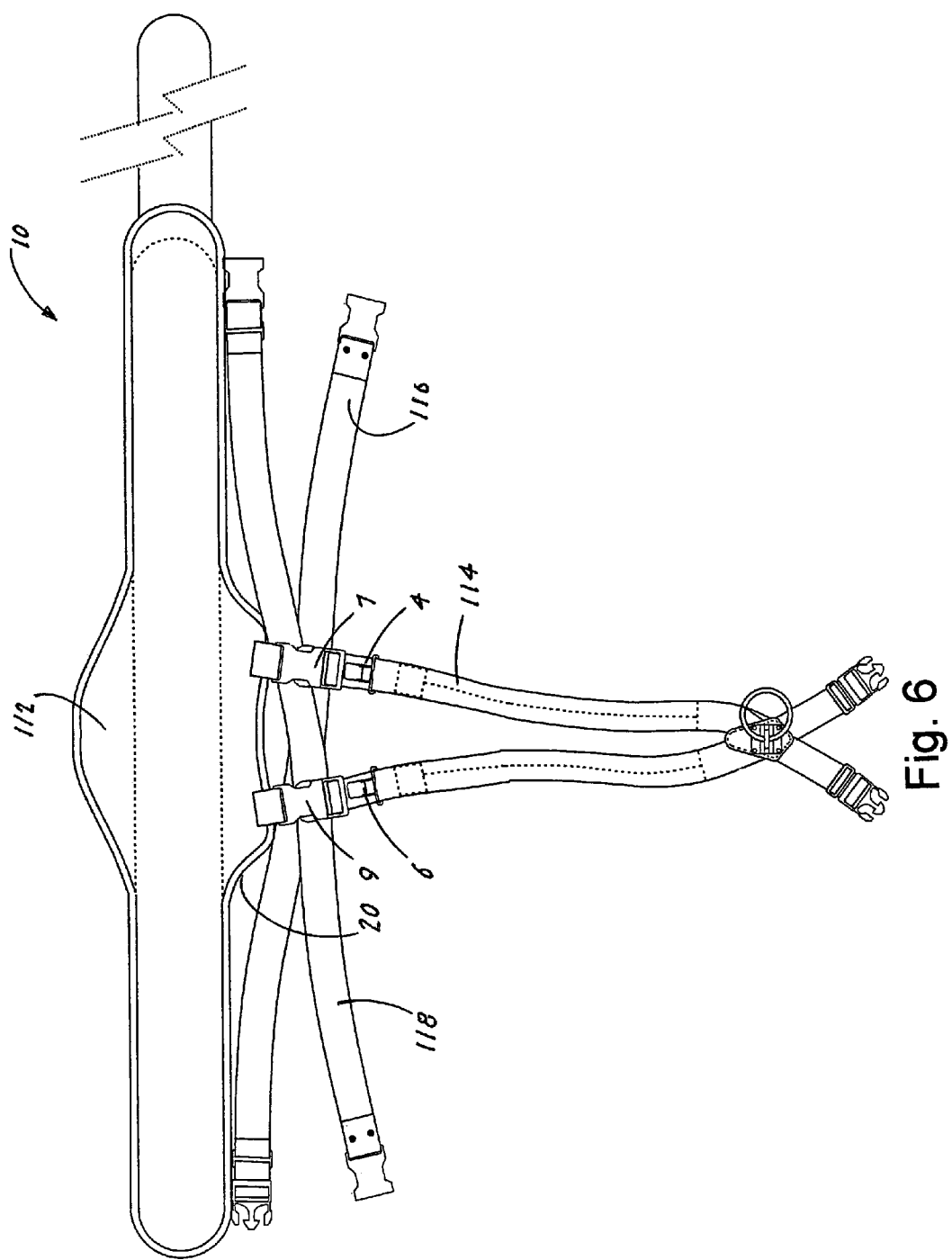
FIG. 6 is a front elevational view of the inner surfaces of the second embodiment of the spinal stretching and decompression device.

The lower support unit 152, as shown in FIGS. 5 and 6, further comprises a buckle designated number 1 and a buckle designed number 4 on a first (right) side support belt 116, and a buckle designated number 2 and a buckle designated number 3 on a second (left) side support belt 118.

In order to assemble the second embodiment of the device 10, the following steps are performed:

1. Prepare base support belt and lower support unit by attaching buckles as with the first embodiment.

2. Attach buckle 3 to buckle 8, buckle 4 to buckle 7, buckle 5 to buckle 10, and buckle 6 to buckle 9.

3. Put base support belt and lower support unit on person.

4. Attach first and second side support belts.

5. Attach buckle A to buckle E, buckle C to buckle F, and buckle B to buckle D.

6. Adjust the device for a secure and comfortable fit.

Additionally, both embodiments can include an area on the base support belt's inner surface 16 for mounting a laser device 126, as shown in FIG. 4. The laser device 126 operates at a frequency of 650 nm. The laser device 126 is removably secured to the inner surface 16 by an attachment means 128 which preferably comprises a hook and loop fastener, although other means such as a nut and bolt combination, double-sided tape can also be utilized.

While the invention has been described in detail and pictorially shown in the accompanying drawings it is not to be limited to such details, since many changes and modifications may be made to the invention without departing from the spirit and the scope thereof. Hence, it is described to cover any and all modifications and forms which may come within the language and scope of the claims.

The invention claimed is:

1. A spinal stretching and decompression device that is worn by a person during an exercise or stretching session, wherein said device is comprised of:
  a) a base support belt having an outer surface, an inner surface, an upper edge, a lower edge, a first end, a second end, a first strap loop, a second strap loop and attachment means,
  b) a lower support unit that is integrally attached to said base support belt and has a first strap, a second strap, a first strap buckle, a second strap buckle, buckle attachment means and a hitch ring assembly comprising a hitch base; a hitch plate, a hitch ring and assembly attachment means, c) a first side support belt having an outer surface, an inner surface, a first buckle, a second buckle and buckle adjustment means, and d) a second side support belt having an outer surface, an inner surface, a first buckle, a second buckle, and buckle adjustment means, wherein said device is attached together and worn by a person to facilitate stretching or decompression of the person's spine, wherein said device can be adjustably tightened or loosened depending on the size of the person or the type of exercise or stretching that is being performed.

2. The spinal stretching and decompression device as specified in claim 1 wherein said belts are made of a material that is selected from the group consisting of nylon, leather, and fabric.

3. The spinal stretching and decompression device as specified in claim 1 wherein said device is worn around a person's mid-section encompassing the person's buttocks and crotch region.

4. The spinal stretching and decompression device as specified in claim 1 wherein the attachment means for attaching the buckles to said straps are comprised of a plurality of nut and bolt combination or rivets.

5. The spinal stretching and decompression device as specified in claim 1 wherein the buckles are comprised of heavy duty, quick-release, snap type.

6. The spinal stretching and decompression device as specified in claim 1 wherein said device is utilized in combination with stretching or exercising actions that are selected from the group consisting of bending, lifting, and extending.

7. The spinal stretching and decompression device as specified in claim 1 wherein the hitch ring assembly attachment means are comprised of a plurality of nuts and bolts.

8. The spinal stretching and decompression device as specified in claim 1 wherein said base support belt further comprising a buckle designated number (3), a buckle designated number (4), a buckle designated number (5), a buckle designated number (6), a buckle designated number (7), a buckle designated number (8), a buckle designated number (9); a buckle designated number (10), and buckle attachment means.

9. The spinal stretching and decompression device as specified in claim 8 wherein said device is worn around a person's mid-section encompassing the person's buttocks and crotch region.

10. The spinal stretching and decompression device as specified in claim 1 wherein said lower support unit further comprising a first buckle and a second buckle on a first side support belt and a first buckle and a second buckle on a second side support belt.

11. The spinal stretching and decompression device as specified in claim 1 further comprising an area on the base support belt's inner surface for mounting a laser device.

12. The spinal stretching and decompression device as specified in claim 11 wherein the laser device operates at 650 nm.

13. The spinal stretching and decompression device as specified in claim 12 wherein the attachment means for securing the laser device is selected from the group consisting of a hook and loop fastener, a nut and bolt combination, and a double-sided tape.

14. The spinal stretching and decompression device as specified in claim 11 wherein the laser device is removably secured to said base support belt by an attachment means.

15. A method for attaching a spinal stretching and decompression device to a person's body, wherein said device is comprised of a plurality of straps having buckles and a plurality of belts having buckles, wherein said method is comprised of the following steps:

a) wrap a base support belt around a person's waist and secure a first end of the belt to a second end by use of an attachment means, b) wrap a first side support belt around the base support belt, wherein the first side support belt has a buckle designated (A) and a buckle designated (B), and is inserted through a first belt loop on the base support belt, c) wrap a second side support belt around the base support belt, wherein the second side support belt has a buckle designated (C) and a buckle designated (D), and is inserted through a second belt loop on the base support belt, d) wrap a lower support unit around and under a person's buttocks and groin, and attach buckle designated (A) to a buckle designated (E), e) attach buckle designated (C) to buckle designated (F), f) attach buckle designated (B) to buckle designated (D), and g) adjust said device for a secure and comfortable at by use of adjustment means.

\* \* \* \* \*